United States Patent [19]

Imamura

[11] Patent Number: 4,908,517
[45] Date of Patent: Mar. 13, 1990

[54] APPARATUS FOR EXAMINING THE SURFACE OF A SUBSTRATE

[75] Inventor: Kazunori Imamura, Tokyo, Japan
[73] Assignee: Nikon Corporation, Tokyo, Japan
[21] Appl. No.: 225,874
[22] Filed: Jul. 29, 1988

[30] Foreign Application Priority Data

Aug. 6, 1987 [JP] Japan .............................. 62-197084

[51] Int. Cl.⁴ .......................................... G01N 21/88
[52] U.S. Cl. .................................. 250/563; 250/236; 250/572; 356/430
[58] Field of Search ............... 250/563, 562, 572, 236, 250/237; 356/430, 237

[56] References Cited

U.S. PATENT DOCUMENTS 4,363,118  12/1982  Roach et al. ...................... 250/572
4,468,120  8/1984   Tanimoto et al. .................. 356/237
4,613,753  9/1986   Okada et al. ..................... 250/236
4,849,645  7/1989   Mendenko et al. ................. 250/563

Primary Examiner—Leon Scott, Jr.
Attorney, Agent, or Firm—Shapiro and Shapiro

[57] ABSTRACT

An apparatus for examining the surface of a substrate comprises irradiating means for supplying a light beam which scans the surface of the substrate, first and second light-receiving means for individually receiving scattered lights travelling in different first and second directions from the surface of the substrate and individually producing first and second output signals conforming to the intensities of the received lights, and means for discriminating the directional characteristics of the scattered lights on the basis of the time phase shift between the first and second output signals.

8 Claims, 6 Drawing Sheets

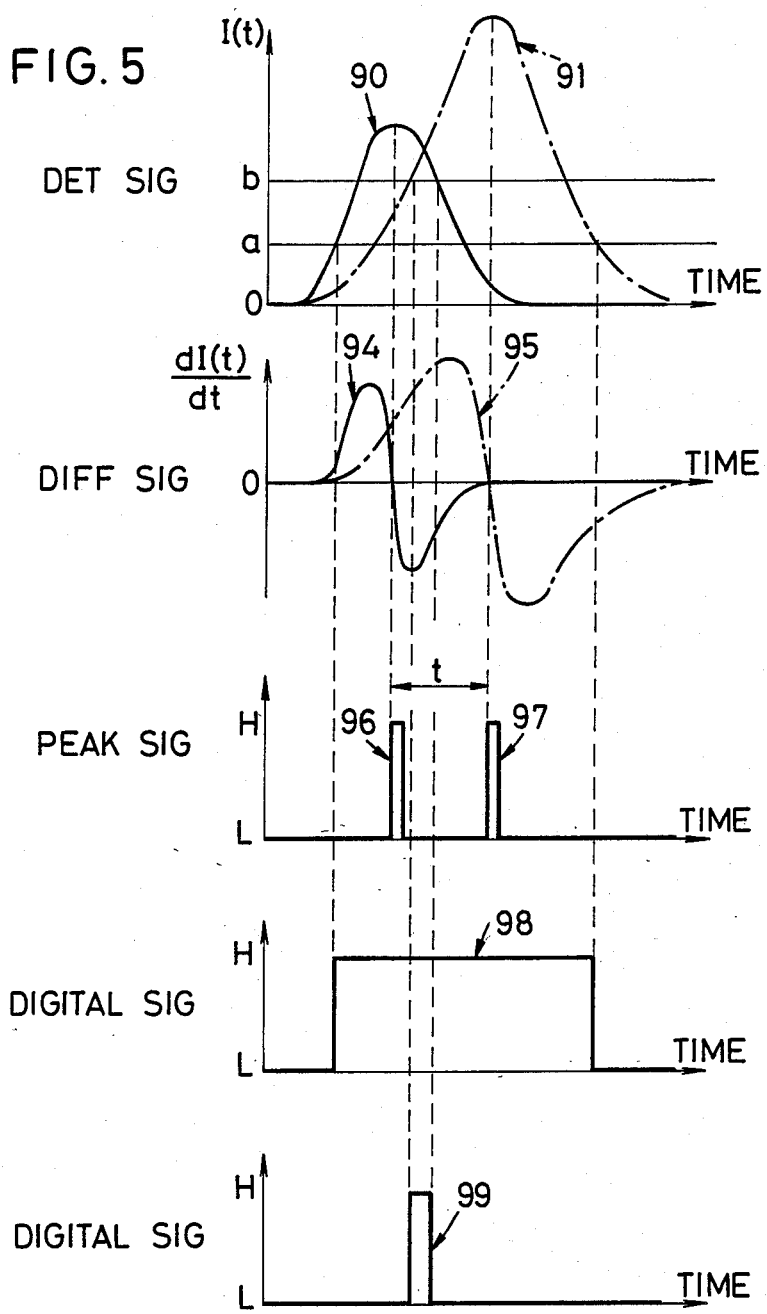

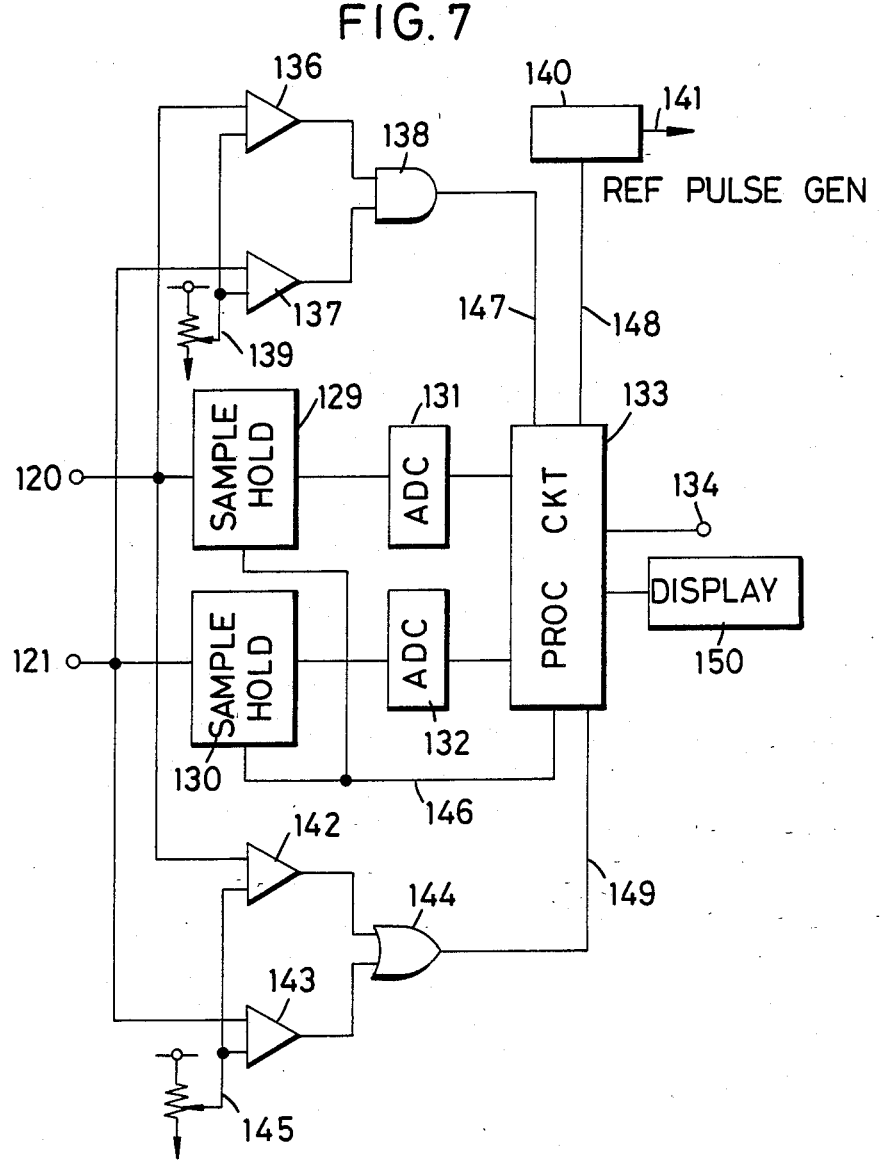

APPARATUS FOR EXAMINING THE SURFACE OF A SUBSTRATE

BACKGROUND OF THE INVENTION

1. Field of the Invention

This invention relates to an apparatus for optically automatically examining the surface of a substrate, and more particularly to an apparatus for automatically detecting a foreign particle such as minute dust adhering to a substrate on which a semiconductive integrated circuit pattern is provided, such as a photomask for LSI, a reticle or a wafer.

2. Related Background Art

As an apparatus of this type, there is known an apparatus in which, as disclosed in U.S. Pat. No. 4,468,120, a laser beam applied to a reticle or the like and the difference between the directional characteristics of scattered lights from a circuit pattern and a foreign particle is utilized to automatically detect only the foreign particle. The principle of this known apparatus is as follows.

When a light beam condensed and stopped down, for example, a laser beam, is applied to the edge portion of a circuit pattern (a thin film layer of chromium or like material) on a substrate, there is created a scattered light of strong directionality having had its directionality determined by the angle of incidence onto the edge. On the other hand, when a foreign particle is present on the surface of the substrate and a laser beam is applied thereto, the scattered light spreads in all directions.

The scattered light thus created is detected by a condensing lens and a photoelectric detector. If a plurality of photoelectric detectors are disposed so as to look into that portion of the substrate to which the laser beam has been applied, from different directions, and their photoelectric outputs are compared, the scattered light from the circuit pattern edge and the scattered light from the foreign particle can be discriminated therebetween.

However, in the prior art as described above, there is no problem when the circuit pattern on the substrate is sufficiently larger than the laser beam spot and when the circuit pattern is of the same size as the laser beam spot, whereas the scattered light from the circuit pattern loses its directionality when the circuit pattern is sufficiently smaller than the laser beam spot, and this has led to the problem that it becomes difficult to discriminate between the circuit pattern and the foreign particle.

SUMMARY OF THE INVENTION

The present invention has as its object to provide an examining apparatus which is capable of discriminating between a foreign particle (an optically heterogeneous medium) and a circuit pattern even on an object to be examined on which the circuit pattern is minutely depicted.

The apparatus of the present invention is provided with a plurality of photoelectric elements for detecting a scattered light created from that portion of the surface of a substrate to which a light beam is applied, in different directions, and means for detecting the time phase shift caused between the outputs of said plurality of photoelectric elements.

BRIEF DESCRIPTION OF THE DRAWINGS

FIG. 5 is a chart showing the wave forms of various signals in the first embodiment of the present invention.

FIG. 7 is a circuit block diagram showing the construction of an electrical processing system according to the second embodiment.

DESCRIPTION OF THE PREFERRED EMBODIMENTS

Figure 1:
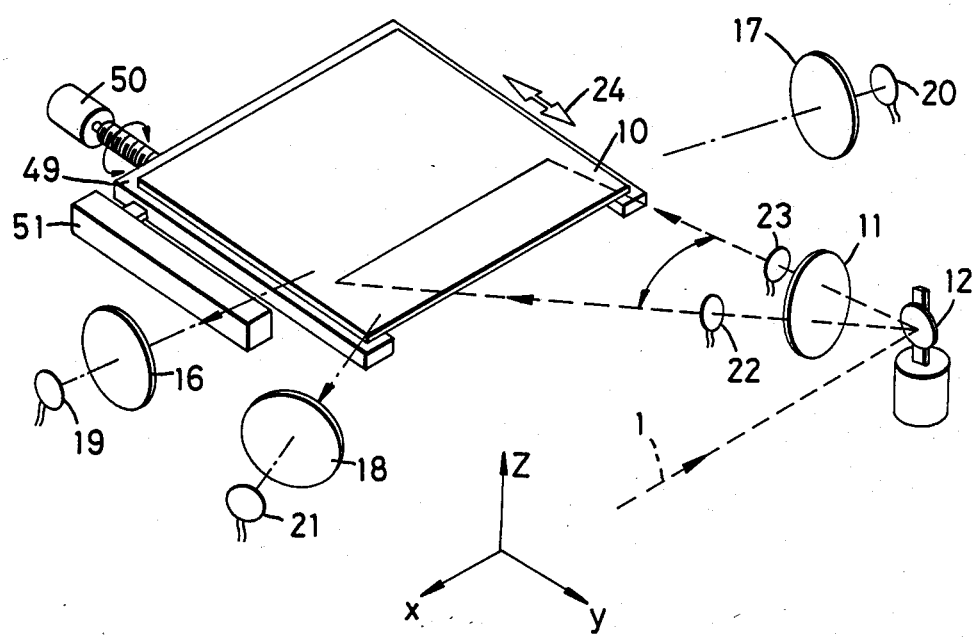
FIG. 1 is a perspective view showing the constructions of the optical system and mechanical system of a heretofore used foreign particle examining apparatus.

FIG. 1 shows the optical construction of an examining apparatus used in an embodiment of the present invention, and this construction itself is shown in the aforementioned U.S. patent. The surface of a substrate 10 such as a reticle including a circuit pattern, a mask or a wafer is on the x-y plane of a coordinates system xyz. A laser light 1 is suitably changed into any beam diameter by an optical member such as a beam expander (not shown) or a condensing lens 11 and increases its light intensity per unit area. The laser light 1 scans the substrate in x direction by a scanner 12 (a vibrator, a galvano mirror or a rotational polygon mirror). The laser light 1 enters the surface of the substrate obliquely thereto (for example, at an angle of incidence of 70°–80°). Accordingly, the shape of the spot of the laser light 1 on the substrate becomes an elliptical shape extending substantially in y direction in the figure. Also, the scanning position of the laser light scanned by the scanner 12 is detected by photoelectric elements 22 and 23. On the other hand, the substrate 10 is placed on a supporting bed 49 and is moved by moving means 50 such as a motor in the direction of arrow 24 substantially orthogonal to the scanning direction of the laser light. The position of application in y direction is measured by a linear encoder 51.

Photoelectric elements 19, 20 and 21 are disposed so as to receive scattered light from the laser spot on the scanning line from different directions. The scattered light is condensed on the light-receiving surfaces of the photoelectric elements 19, 20 and 21 by condensing lenses 16, 17 and 18. The condensing lenses 16, 17 and 18 are disposed so that their optic axes are oblique to the surface of the substrate, i.e., x-y plane. This is for the purpose of making the angles of the optic axes with respect to x-y plane small (e.g. 10°–45°) and making it difficult for the condensing lenses to be affected by the irregular reflection or the like of the pattern surface itself of the substrate. In this example of the apparatus, the photoelectric elements 19, 20 and 21 move on the substrate on x-y plane in y direction while scanning the laser light by the scanner 12. When during this movement, the laser spot is on the edge of the pattern, the scattered light is accompanied by strong directionality as previously described. So, of the photoelectric elements 19, 20 and 21 capable of detecting the scattered light from different directions, only a particular photoelectric element receives the scattered light from the edge. Accordingly, the disposition of the photoelectric elements is determined so that they do not receive the scattered light from the edge of the pattern at the same time. Also, when the laser spot is on a foreign particle, the scattered light by the foreign particle is produced in every direction, i.e., substantially without directionality. Accordingly, in such case, all the photoelectric elements 19, 20 and 21 receive the scattered light from the foreign particle. Further, when a foreign particle is present near the edge of the pattern, the scattered light from the edge is received by a particular photoelectric element and the scattered light from the foreign particle is received by all the photoelectric elements. In this case, the photoelectric output signals of the photoelectric elements assume different values depending on the angle of incidence of the laser light onto the edge (or onto the surface) and the size of the foreign particle.

So the photoelectric output signals of the photoelectric elements 19, 20 and 21 are suitably amplified by amplifiers, whereafter the output signals thereof are compared with a predetermined reference signal (for example, a slice level).

Figure 2:
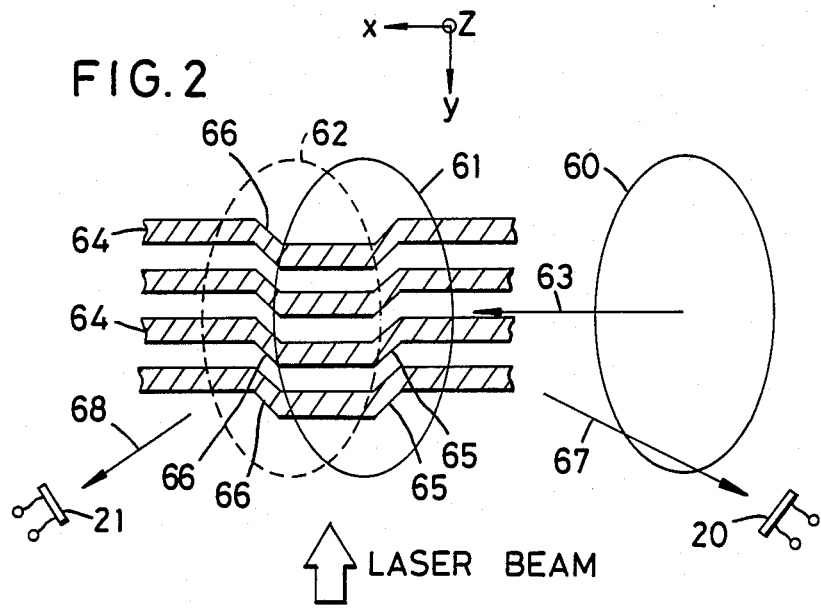
FIGS. 2 and 3 illustrate the scattering phenomena caused by complicated minute circuit patterns.

Here, the phenomenon of scattering when a laser beam is applied to a circuit pattern on a substrate will be considered. In FIG. 2, a minute circuit pattern 64 on a substrate lying on x-y plane is a light-intercepting substance having a thickness of 0.05–2.0 μm, and scattered lights or diffracted lights 67 and 68 are emitted in the directions of arrows, respectively, by pattern edges 65 and 66 oblique (e.g., 45°) with respect to x-y direction. A laser spot 60 is moved on the substrate in the direction of arrow 63 by the scanner 12 of FIG. 1. When the laser spot is at a position 61, the pattern edge 65 comes substantially to the center of the laser spot and the scattered light 68 is emitted most intensely, and the intensity of the photoelectric signal detected from the photoelectric element 20 also becomes maximum at this time. At this time, the scattered light 68 is emitted weakly as compared with the scattered light 67, and the intensity of the photoelectric signal detected from the photoelectric element 21 is also smaller than that of the photoelectric signal from the photoelectric element 20.

As time passes, the laser spot comes to a position 62, but at this time, the pattern edge 66 lies substantially at the center of the laser spot and therefore, the intensity of the photoelectric signal from the photoelectric element 20 reduces and the intensity of the photoelectric signal from the photoelectric element 21 rises to a maximum signal intensity.

As time further passes, the laser spot deviates from a circuit pattern which emits the scattered light 68 or 70 and therefore, no great photoelectric signals are produced in the photoelectric elements 20 and 21.

On the other hand, a foreign particle is generally smaller than the diameter of the laser spot and the spatial distance as between the pattern edges 65 and 66 can be neglected and therefore, the scattered lights 67 and 68 are emitted most intensely when the foreign particle is substantially at the center of the laser spot, and the photoelectric signals from the photoelectric elements 20 and 21 become maximum in intensity at the same time.

From the foregoing, it can be understood that when the laser beam has been scanned, a time phase difference occurs between the maximum signals of the two photoelectric elements based on the scattered light from the pattern edge and the maximum signals of the two photoelectric elements based on the scattered light from the foreign particle are produced at the same time.

If use is thus made of the difference between the times when the maximum signals are obtained, i.e., the time phase difference, it becomes possible to automatically discriminate between the scattered light from the pattern edge and the scattered light from the foreign particle.

Figure 3:
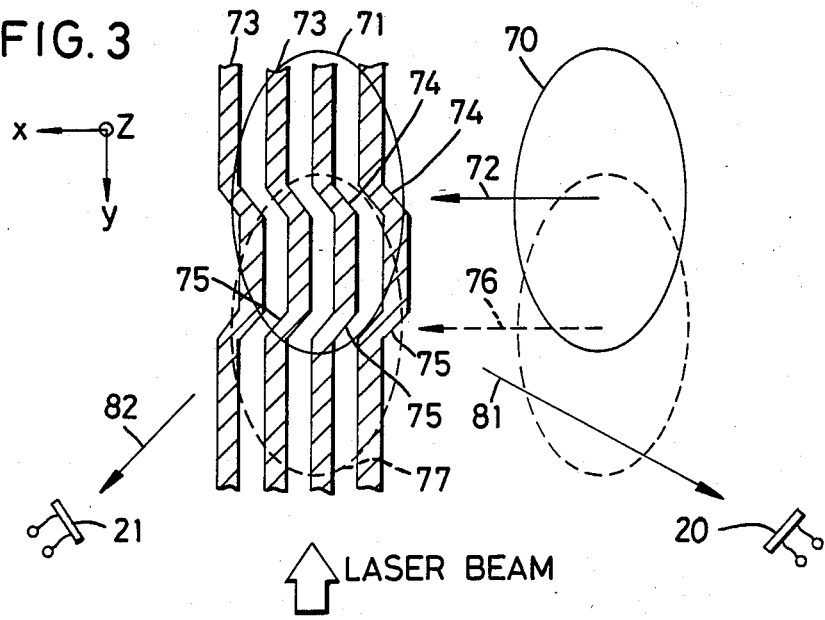

Reference is now had to FIG. 3 to describe an example of the case where another circuit pattern 73 is formed. When a laser spot 70 is scanned in the direction of arrow 72 and crosses a circuit pattern 73, a pattern edge 74 corresponds to the central portion of the laser spot 71 and therefore, scattered light or diffracted light 82 is emitted most intensely. Also, scattered light or diffracted light 81 of low intensity is emitted from a pattern edge 75.

The substrate is moved in y direction and the laser spot moves in the direction of arrow 76 along the next scanning line or the scanning line after a plurality of scanning lines, and at a position 77, the pattern edge 75 comes to the center of the laser spot. Thereby, the scattered light 81 is emitted most intensely and the other scattered light 82 is emitted weakly.

Consequently, the intensities of the scattered lights which arrive at the photoelectric elements 20 and 21 becomes maximum at different times.

Figure 4:
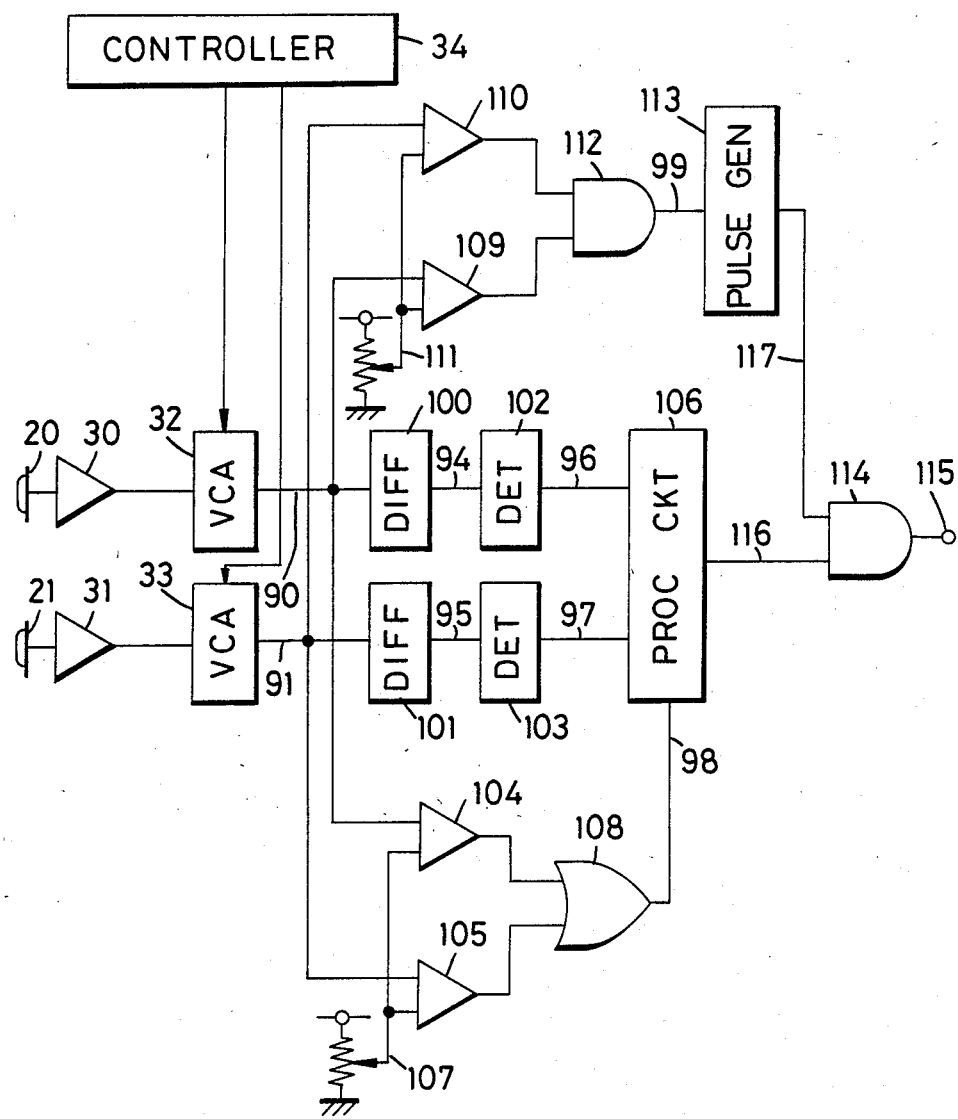
FIG. 4 is a circuit block diagram showing the construction of the electrical processing system of a defect examining apparatus according to a first embodiment of the present invention.

FIG. 4 shows an electric circuit for processing the photoelectric outputs of the photoelectric elements 20 and 21.

The outputs of the photoelectric elements 20 and 21 are amplified by amplifiers 30 and 31 and input to VCA's 32 and 33. VCA's 32 and 33, as shown in U.S. Pat. No. 4,468,120, are gain-controlled by a controller 34 in conformity with the disposition of the photoelectric elements 20 and 21 relative to the position of the laser spot on the scanning line.

Detection signals 90 and 91 from the VCA's 32 and 33 are time-differentiated by differentiating circuits 100 and 101, respectively, and are further input to zero cross detecting circuits 102 and 103, respectively, which produce electric pulses (peak signals) 96 and 97 in zero cross portions on the differentiated wave forms. These peak signals 96 and 97 are input to a processing circuit 106. The threshold a of FIG. 5 is input as a threshold voltage 107 to comparators 104 and 105, and the detection signals 90 and 91 are input to the other terminals of the comparators.

The comparators 104 and 105 output Hi level digital signals when the detection signals 90 and 91 are greater than the threshold voltage 107. These two signals are input to an OR (logic sum) circuit 108 and input to the processing circuit 106 as a digital signal 98 as shown in FIG. 5.

On the ohter hand, the threshold b shown in FIG. 5 is input as a threshold voltage 111 to one terminal of each comparator 109, 110, and the detection signals 90 and 91 are input to the other terminals of these comparators. The comparators 109 and 110 output Hi level digital signals when the detection signals 90 and 91 are greater than the threshold voltage 111. These two signals are input to an AND (logic product) circuit 112 and converted into a digital signal 99 as shown in FIG. 5. This signal 99 is a foreign particle detection signal in the prior-art apparatus. This signal is input to a pulse generator 113 and becomes a binarized pulse of a suitable pulse time width and is input to an AND circuit 114. This AND circuit 114 outputs a digital signal 115 which will assume Hi level when only a foreign particle is detected.

Operation of the electric circuit of FIG. 4 will now be described.

The peak signals 96 and 97 output from the detecting circuits 102 and 103, with a digital signal 98 produced when the photoelectric element 20 or 21 is receiving the scattered light, are input to the processing circuit 106. With this digital signal 98 as the gate input, that is, during the time that the digital signal 98 is at Hi level, the processing cirucit 106 measures the time difference t between the peak signals 96 and 97. When this time difference is smaller than a predetermined value, the processing circuit 106 outputs a Hi level signal 116 to the AND circuit 114. On the other hand, when the time difference is greater than the predetermined value and when the gate input (the digital signal 98) is at Lo level, the processing circuit 106 outputs a Lo level signal 116 to the AND circuit 114. On the other hand, a foreign particle detection signal similar to that in the prior-art apparatus is output as a Hi level digital signal 99 from the AND circuit 112, and as can be seen in FIG. 5, in some cases, the time when this signal is output is earlier than the peak signlas 96 and 97, but at least this signal is not produced at a point of time later than the peak signals 96 and 97. So, during the time that the processing circuit 106 is determining the magnitude of the time difference t (exactly, during the time until the signal 116 is produced), this foreign particle detection signal is kept at Hi level and therefore, by the pulse generator 113, it is converted into a signal 117 in which the pulse width of the digital signal 99 has been extended by a predetermined time.

Now, the foreign particle detection signal 117 and the signal 116 conforming to the result of the detection of the time difference between the two scatter signals are input to the AND circuit 114, and when the signals 116 and 117 are both at Hi level, the AND circuit 114 outputs a Hi level signal 115. On the other hand, when the foreign particle detection signal 117 is at Hi level but there is a time difference of a predetermined value or greater between the scatter signals, the signal 116 is at Lo level and therefore, it is judged as the scattered light or the diffracted light from the circuit pattern and the signal 115 assumes Lo level. Thus, in the present embodiment, attention is paid to the simultaneousness of the scattered lights from foreign particles and an examining apparatus which is higher in detection rate than the prior-art apparatus can be provided.

Although in the present embodiment, use is made of scatter signals from two directions, a similar effect may be obtained even if scatter signals from three or more directions are used, and in such case, the measurement of the time difference t by the processing circuit 106 can be accomplished by measuring the maximum time difference between three peak signals.

A second embodiment of the present invention will now be described. This embodiment has been instrumented on the basis of the principle shown in FIG. 3. FIGS. 6A-6F show examples of the electrical signals for illustrating the second embodiment of the present invention, and the scattered light or the diffracted light from the circuit pattern 73 of FIG. 3 is received by the photoelectric elements 20 and 21 and becomes electrical signals in which the scanning time t of the laser beam is plotted as the horizontal axis, like detection signals 120 and 121. In FIG. 6, the vertical axis represents the levels of the detection signals 120 and 121. According to the apparatus shown in FIG. 1, during the time that the laser beam moves in x direction, the substrate including the circuit pattern 73 moves in y direction at a low speed and therefore, when the laser beam again crosses the circuit pattern 73, the intensities of the detection signals 120 and 121 differ in shape from those during the previous scanning. FIGS. 6A-6F each show the wave forms of the detection signals during each scanning of the laser beam in x direction, and FIGS. 6A to 6F time-serially show the variations in the wave forms of the detection signals by the variation in the scanning position in y direction. The thresholds a and b in FIGS. 6A-6F are similar to the thresholds a and b in FIG. 5. According to these threshold levels, it is seen that up to the scanning positions of FIGS. 6A-6E, one of the detection signals 120 and 121 exceeds the threshold a and at the scanning position of FIG. 6C, both of the detection signals 120 and 121 exceed the threshold b. So, within one scanning time in x direction, a detection signal monitoring start time $t_1$ and a detection signal monitoring end time $t_2$ are determined, and the space between $t_1$ and $t_2$ is defined as an area for monitoring the variation with time in the detection signals which is called a window. It is to be understood that this window is set from the scanning position next to the scanning position of FIG. 6C in which both of the detection signals 120 and 121 exceed the threshold b, and continues up to the scanning position of FIG. 6F in which neither of the detection signals 120 and 121 exceeds the threshold a.

Here, the timings of the start time $t_1$ and the end time $t_2$ are determined in synchronism with the scanning of the laser beam in x direction, and these timings are such that the time when the detection signal during the scanning position of FIG. 6C has been produced is memorized and during the next scanning, the time earlier by a predetermined amount than that time is defined as $t_1$ and the time later by the predetermined amount than that time is defined as $t_2$.

FIG. 7 shows the electric circuit of the second embodiment of the present invention. The diffracted lights received by the photoelectric elements 20 and 21 are input as detection signals 120 and 121 which have been corrected in their amplification degrees in conformity with the scanning position in x derection. These detection signals 120 and 121 have their maximum values, extracted by sampling and holding circuits 129 and 130, digitalized by A/D converters 131 and 132, and time-serially stored in the storage area of a processing circuit 133.

The detection signals 120 and 121 input to comparators 142 and 143 are compared with a threshold voltage 145 corresponding to the threshold a, and if the detection signals exceed the threshold voltage 145, the comparators 142 and 143 output Hi level signals. The outputs of these comparators 142 and 143 are input to an OR circuit 144, and a digital signal 149 which is the result of the logic sum thereof is input to the processing circuit 133.

Also, comparators 136 and 137 compare the detection signals 120 and 121 with a threshold voltage 139 corresponding to the threshold b, and if the detection signals 120 and 121 exceed the threshold voltage 139, the comparators 136 and 137 output Hi level signals to an AND circuit 138.

Here, if a digital signal 147 which is the result of the calculation of the logic sum by the AND circuit 138 is at Hi level, it would have been recognized as the detection of a foreign particle in the prior-art apparatus. This digital signal 147 is also input to the processing circuit 133. On the other hand, from a reference pulse generator 140 which effects the scanning of the laser beam in x direction, a reference pulse 148 synchronized with the scanning is input to the processing circuit 133, and the window and the scanning position in y direction are counted.

The table below shows the states of the signals in the second embodiment and the operation of the processing circuit 133.

TABLE

Figure 6A:
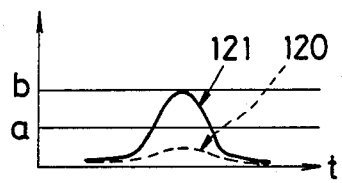
FIGS. 6A–6F are charts showing the variations with time in the photoelectric signals in a second embodiment of the present invention.
Figure 6B:
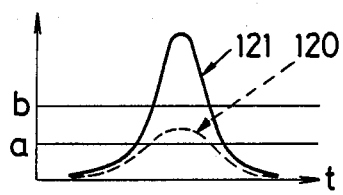
Figure 6C:
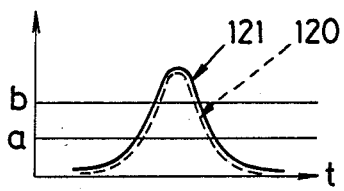
Figure 6D:
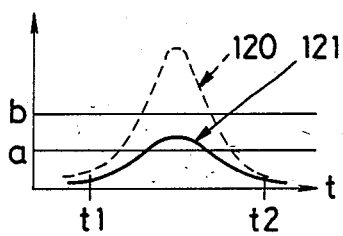
Figure 6E:
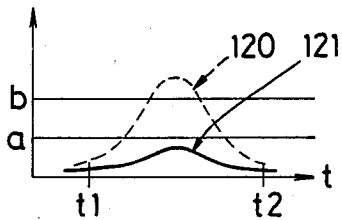
Figure 6F:
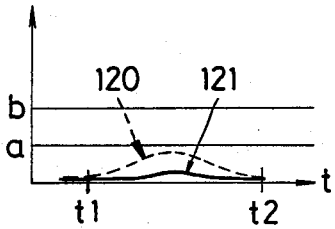

| y-SCAN POS | AND | OR | WINDOW | EXOR | DET |
|---|---|---|---|---|---|
| FIG. 6A | L | H | — | (L) | — |
| FIG. 6B | L | H | — | (L) | — |
| FIG. 6C | H | H | — | (L) | — |
| FIG. 6D | L | H | SET | H | — |
| FIG. 6E | L | H | SET | L | — |
| FIG. 6F | L | L | — | L | PATT |

In the table above, the column of AND shows that the digital signal 147 assumes a high level when in the scanning position of FIG. 6C. The column of OR shows that the digital signal 149 assumes a high level when in the scanning positions of FIGS. 6A–6E. The column of WINDOW shows that the window area determined at the detection signal monitoring start time $t_1$ and the detection signal monitoring end time $t_2$ is set, and is set within the processing circuit 133 after the column of AND (signal 147) has assumed Hi level and only when the column of OR (signal 149) assumes Hi level. In the second embodiment, the various operations by the processing circuit 133 are effected during the scanning in y direction while the WINDOW is set.

The signals shown in the column of EXOR (exclusive or) are made within the processing circuit 133, and assume Lo level when the memorized crest values of the detection signals 120 and 121 are compared with the crest values during the next scanning in x direction and the increase or decrease in the crest values is equal between the detection signals 120 and 121, and assume Hi level when the increase or decrease in the crest values differs between the detection signals 120 and 121. The column of DET (detect) displays the result when only a fine particle has been finally automatically detected when the scanning position in y direction has progressed to FIG. 6F, and in this table, it represents that no foreign particle exists, because it is judged as the pattern portion.

Operation of the second embodiment will now be described. If there is the circuit pattern 73 as described with respect to the principle shown in FIG. 3, scattered lights or diffracted lights 81 and 82 leaving it are received by the photoelectric elements 20 and 21, respectively, and are photoelectrically converted thereby, whereafter detection signals 120 and 121 whose detection sensitivity has been corrected are obtained as in the circuit of FIG. 4. These signals 120 and 121 are varied in their intensities each time the substrate is moved in y direction. The scattered lights then received by the photoelectric elements 20 and 21 are from different pattern edges 75 and 74 and therefore have maximum values at different scanning positions in y direction. The detection signal 121 becomes maximum at the scanning position of FIG. 6B, while the other detection signal 120 becomes maximum at the scanning position of FIG. 6D. In some cases, the increase or decrease in the intensities of these detection signals 120 and 121 varies monotonously, and in some cases, the increase or decrease is repeated during several to several tens of cycles of scanning and the detection signals become maximum at a plurality of scanning positions.

Here, the crest values of those detection signals at each scanning position in y direction are stored in the processing circuit 133 through the A/D converters 131 and 132, and if there is a time difference in the increase or decrease therein, it can be judged as the circuit pattern, and if there is no time difference, it can be judged as a foreign particle.

Now, at the scanning position shown in FIG. 6C, in the prior-art apparatus, both of the two detection signals 120 and 121 exceed the threshold b and therefore, this is regarded as the detection of a foreign particle. At this time, the Hi level of the digital signal 147 is input to the processing circuit 133. The processing circuit 133 always receives as an input a reference pulse 148 synchronized with scanning and monitors the x direction, the position and the scanning No. of laser beam.

Now, the column of AND in the table above assumes Hi level, the processing circuit 133 immediately outputs a high lelvel gate signal 146 to the sampling and holding circuits 129 and 130. This gate signal 146 corresponds to the WINDOW, and the crest values of the detection signals during the time $t_1$ to $t_2$ are digitalized by the A/D converters 131 and 132 and are time-serially stored in the storage area of the processing circuit 133. This WINDOW cannot occur in its perfect form at the scanning position of FIG. 6C, but even when the AND circuit 138 outputs Hi level, the gate signal 146 is output to the sampling and holding circuits 129 and 130 and therefore, the then crest value is also stored. When both of the detection signals 120 and 121 become lower than the threshold a, the processing circuit 133 judges that the digital signal 149 has assume Lo level, and changes the output of the gate signal 146 to low.

From the variations in the crest values of the detection signals 120 and 121 at each scanning position input to the processing circuit 133, it is detected that as shown in the column of EXOR, the increase or decrease in the crest values differs between the detection signals 120 and 121 at the scanning positions of FIGS. 6C and 6D. The processing circuit 133 outputs a Hi level decision signal 134, and judges that no foreign particle is present as the result of the foreign particle examination.

In contrast, in the case of a truely foreign particle, the output of EXOR maintains a low level during the time that it monitors as WINDOW. At that time, the decision signal 134 assumes Lo level. In that case, the processing circuit 133 outputs to a display device 150 a signal of a level conforming to the crest value, and causes the display device to display the size or the like of the foreign particle.

As regards the setting of WINDOW, besides the method of determining it by the digital signal 149, it can also be determined by counting the scanning positions in y direction because the processing circuit 133 receives the digital signal 147 as an input. That is, since the diameter and the amount of movement in y direction of the laser beam are already determined, whether the laser beam deviates from that portion of the circuit pattern which could already be error-detected can be known by counting how many times the beam scanning in x direction has been effected. So, the number of times of scanning can be preset and the judgment of WINDOW can be done on the basis of the count value thereof. Also, the WINDOW setting by the number of times of scanning and the WINDOW by the digital signal 149 can be judged to detect which WINDOW is closed earlier, and that WINDOW which has been closed earlier can be adopted.

In the above-described two embodiments, description has been made with respect to the increase or decrease in the detection signals of two photoelectric elements, but it is apparent that this also entirely holds true of an examining apparatus having three or more photoelectric elements. In such case, if for example, as EXOR in the table above, the increase or decrease in the crest values of a plurality of detection signals is identical during the time that it assumes Hi level in the column of OR in the table above, it is judged as being a foreign particle, and if said increase or decrease differs, it is judged as being not a foreign particle.

There is a case where the crest values of the detection signals 120 and 121 at each scanning position in y direction are identical depending on the shape or the like of the circuit pattern, and in such case, it may be deemed that in the processing circuit 133, the increase or decrease in the crest values is equal between the detection signals 120 and 121, and the apparatus can be programmed in advance such that Lo level is dealt with as EXOR. Of course, if the increase or decrease in the crest values of the detection signals 120 and 121 in which other WINDOW is judged as occurring is equal, such detection signals 120 and 121 are collectively judged as being due to a foreign particle, and if the increase or decrease in said crest values is not equal, such detection signals 120 and 121 are collectively judged as being due to the pattern.

The display of the result of the detection, etc. may be accomplished by carrying out a method similar to that carried out in the prior-art apparatus and therefore need not be described herein.

Further, as shown in the aforementioned U.S. patent, the direction of incidence of the laser beam and the light-receiving system may be disposed with the body to be examined interposed therebetween.

I claim:

1. An apparatus for examining the surface of a substrate, comprising:
   irradiating means for supplying a light beam which scans the surface of said substrate;
   first and second light-receiving means for individually receiving scattered lights travelling in different first and second directions from the surface of said substrate and individually producing first and second output signals conforming to the intensities of the received lights; and
   means for discriminating the directional characteristics of said scattered lights on the basis of the time phase shift between said first and second output signals.

2. An apparatus according to claim 1, wherein said discriminating means judges that the directionality of said scattered lights is great when the time phase shift between said first and second output signals is greater than a reference value, and judges that the directionality of said scattered lights is small when said time phase shift is smaller than said reference value.

3. An apparatus according to claim 2, wherein said discriminating means includes means for detecting the time difference when said first and second output signals exhibit their respective peaks, and judges that the directionality of said scattered lights is small when said detected time difference is shorter than a reference time.

4. An apparatus for detecting a foreign particle present on the surface of substrate, comprising:
   means for supplying a light beam which scans the surface of said substrate;
   first and second light-receiving means for individually receiving scattered lights travelling in different first and second directions from the surface of said substrate and individually producing first and second output signals conforming to the intensities of the received lights;
   means for discriminating the directional characteristics of said scattered lights on the basis of the time phase shift between said first and second output signals; and
   means for determining the presence of said foreign particle on the basis of said first and second output signals and the directional characteristics of said scattered lights.

5. An apparatus according to claim 4, wherein said discriminating means detects the time difference when said first and second output signals exhibit their respective peaks, and judges that the directionality of said scattered lights is small when said time difference is shorter than a reference time.

6. An apparatus according to claim 5, wherein said determining means determines the presence of said foreign particle when both of said first and second output signals exceed a threshold level and it is judged by said discriminating means that the directionality of said scattered lights is small.

7. An apparatus for examining the surface of a substrate, comprising:
   irradiating means for supplying a light beam which scans the surface of said substrate along scanning lines;
   first and second light-receiving means for individually receiving scattered lights travelling in different first and second directions from the surface of said substrate and individually producing first and second output signals conforming to the intensities of the received lights; and
   means for discriminating the directional characteristics of said scattered lights on the basis of the difference between the variation of said first output signal occuring during successive scans of said light beam along said scanning lines and the variation of said second output signal occurring during successive scans of said light beam along said scanning lines.

8. An apparatus according to claim 7 further comprising means for determining the presence of a foreign particle on the surface of said substrate on the basis of said first and second output signals and the directional characteristics of said scattered lights.

* * * * *